(12) United States Patent
Baskis

(10) Patent No.: US 12,649,140 B2
(45) Date of Patent: Jun. 9, 2026

(54) CHEMICAL REFORMER SYSTEMS AND METHODS

(71) Applicant: Paul Baskis, Oakland, KY (US)

(72) Inventor: Paul Baskis, Oakland, KY (US)

( * ) Notice: Subject to any disclaimer, the term of this patent is extended or adjusted under 35 U.S.C. 154(b) by 1088 days.

(21) Appl. No.: 17/710,618

(22) Filed: Mar. 31, 2022

(65) Prior Publication Data

US 2022/0314192 A1 Oct. 6, 2022

Related U.S. Application Data

(60) Provisional application No. 63/168,332, filed on Mar. 31, 2021.

(51) Int. Cl.
| | |
|---|---|
| *B01D 3/14* | (2006.01) |
| *B01J 19/00* | (2006.01) |
| *B01J 19/24* | (2006.01) |
| *B01J 49/90* | (2017.01) |
| *C12M 1/00* | (2006.01) |
| *C12M 1/34* | (2006.01) |
| *C12M 1/36* | (2006.01) |

(52) U.S. Cl.
CPC ............ *B01J 19/245* (2013.01); *B01D 3/143* (2013.01); *B01J 19/0013* (2013.01); *C12M 41/12* (2013.01); *C12M 41/40* (2013.01);

*C12M 41/48* (2013.01); *C12M 43/00* (2013.01); *B01J 2219/00051* (2013.01); *B01J 2219/00162* (2013.01)

(58) Field of Classification Search
CPC ........ B01D 3/12; B01D 3/143; B01J 19/0013; B01J 19/245; B01J 2219/00051; B01J 2219/00162; C12M 41/12; C12M 41/40; C12M 41/48; C12M 43/00
See application file for complete search history.

(56) References Cited

U.S. PATENT DOCUMENTS

| | | | | | |
|---|---|---|---|---|---|
| 5,104,419 | A | * | 4/1992 | Funk ...................... | C10K 1/026 |
| | | | | | 518/703 |
| 2019/0211269 | A1 | * | 7/2019 | Galloway .............. | C10K 1/024 |

* cited by examiner

*Primary Examiner* — Lydia Edwards

(74) *Attorney, Agent, or Firm* — Roy Chan; Stoyanov Law PLLC

(57) ABSTRACT

A chemical reformer system has an inlet, a digester, a series of chemical reformers, coolers and separators. The temperatures and pressures of the digester and chemical reformers may be regulated, where the pressure decreases from the first chemical reformer to the last and the temperature increases from the first chemical reformer to the last. The chemical reformer system may be utilized to convert feedstock biomass to output compounds, such as bio-oils.

9 Claims, 3 Drawing Sheets

CHEMICAL REFORMER SYSTEMS AND METHODS

CROSS-REFERENCE TO RELATED APPLICATIONS

This application claims priority to U.S. Provisional Application No. 63/168,332, filed Mar. 31, 2021, which is hereby incorporated by reference in its entirety.

STATEMENT REGARDING FEDERALLY SPONSORED RESEARCH OR DEVELOPMENT

Not Applicable

REFERENCE TO SEQUENCE LISTING A TABLE OR A COMPUTER PROGRAM LISTING COMPACT DISC APPENDIX

Not Applicable

BACKGROUND OF THE INVENTION

The present invention is related to chemical reformers used to convert feedstock biomass into output compounds, such as bio-oils.

BRIEF SUMMARY OF THE INVENTION

In an embodiment of the present invention, a chemical reformer system comprises an inlet, a digester, a digester pressure regulator, a digester temperature regulator, a digester-first chemical reformer connector, a first chemical reformer, a first chemical reformer-second chemical reformer connector, a second chemical reformer, a second chemical reformer-third chemical reformer connector, a third chemical reformer, a first cooler, a first chemical reformer-first cooler connector, a second chemical reformer-first cooler connector, a third chemical reformer-first cooler connector, a first separator, a first cooler-first separator connector, a first separator vapor outlet, a first separator nonpolar outlet, a first separator polar outlet, a second cooler, a third chemical reformer-second cooler connector, a second separator, a second cooler-second separator connector, a second separator light nonpolar outlet, a second separator medium nonpolar outlet, a second separator heavy nonpolar outlet, a second separator polar outlet, and a first separator-second separator connector. The first chemical reformer comprises a first chemical reformer top portion, a first chemical reformer bottom portion, a first chemical reformer pressure regulator, and a first chemical reformer temperature regulator. The second chemical reformer comprises a second chemical reformer top portion, a second chemical reformer bottom portion, a second chemical reformer pressure regulator, and a second chemical reformer temperature regulator. The third chemical reformer comprises a third chemical reformer top portion, a third chemical reformer bottom portion, a third chemical reformer pressure regulator, and a third chemical reformer temperature regulator. The first separator comprises a first separator top portion, a first separator middle portion, and a first separator bottom portion. The second separator comprises a second separator top portion, a second separator middle portion, a second separator bottom portion, and a second separator residual portion. The inlet receives feedstock and is in fluid communication with the digester, which is in fluid communication with the first chemical reformer through the digester-first chemical reformer connector. The first chemical reformer bottom portion is in fluid communication with the second chemical reformer bottom portion through the first chemical reformer-second chemical reformer connector. The first chemical reformer top portion is in fluid communication with the first cooler through the first chemical reformer-first cooler connector. The second chemical reformer bottom portion is in fluid communication with the third chemical reformer bottom portion through the second chemical reformer-third chemical reformer connector. The second chemical reformer top portion is in fluid communication with the first cooler through the second chemical reformer-first cooler connector. The third chemical reformer top portion is in fluid communication with the first cooler through the third chemical reformer-first cooler connector. The first cooler is in fluid communication with the first separator through the first cooler-first separator connector. The first separator top portion is in fluid communication with the first separator vapor outlet. The first separator middle portion is in fluid communication with the first separator nonpolar outlet. The first separator bottom portion is in fluid communication with the first separator polar outlet. The third chemical reformer is in fluid communication with the second cooler through the third chemical reformer-second cooler connector. The second cooler is in fluid communication with the second separator through the second cooler-second separator connector. The second separator top portion is in fluid communication with the second separator light nonpolar outlet. The second separator middle portion is in fluid communication with the second separator medium nonpolar outlet. The second separator bottom portion is in fluid communication with the second separator heavy nonpolar outlet. The second separator residual portion is in fluid communication with the second separator polar outlet.

In another embodiment of the present invention, the chemical reformer system further comprises a control system. The control system is configured to control a digester pressure through the digester pressure regulator. The control system is configured to control a digester temperature through the digester temperature regulator. The control system is configured to control a first chemical reformer pressure through the first chemical reformer pressure regulator. The control system is configured to control a first chemical reformer temperature through the first chemical reformer temperature regulator. The control system is configured to control a second chemical reformer pressure through the second chemical reformer pressure regulator. The control system is configured to control a second chemical reformer temperature through the second chemical reformer temperature regulator. The control system is configured to control a third chemical reformer pressure through the third chemical reformer pressure regulator. The control system is configured to control a third chemical reformer temperature through the third chemical reformer temperature regulator.

In yet another embodiment of the present invention, the first chemical reformer pressure is greater than the second chemical reformer pressure. The second chemical reformer pressure is greater than the third chemical reformer pressure. The first chemical reformer chemical reformer temperature is less than the second chemical reformer temperature. The second chemical reformer temperature is less than the third chemical reformer temperature.

In an embodiment of the present invention, a chemical reformer system comprises an inlet, a first chemical reformer, a first chemical reformer-second chemical reformer connector, a second chemical reformer, a second chemical reformer-third chemical reformer connector, a third chemical reformer, a first cooler, a first chemical reformer-first cooler connector, a second chemical reformer-first cooler connector, a third chemical reformer-first cooler connector, a first separator, a first cooler-first separator connector, a first separator vapor outlet, a first separator nonpolar outlet, a first separator polar outlet, a second cooler, a third chemical reformer-second cooler connector, a second separator, a second cooler-second separator connector, a second separator light nonpolar outlet, a second separator medium nonpolar outlet, a second separator heavy nonpolar outlet, and a first separator-second separator connector. The first chemical reformer comprises a first chemical reformer top portion, a first chemical reformer bottom portion, a first chemical reformer pressure regulator, and a first chemical reformer temperature regulator. The second chemical reformer comprises a second chemical reformer top portion, a second chemical reformer bottom portion, a second chemical reformer pressure regulator, and a second chemical reformer temperature regulator. The third chemical reformer comprises a third chemical reformer top portion, a third chemical reformer bottom portion, a third chemical reformer pressure regulator, and a third chemical reformer temperature regulator. The first separator comprises a first separator top portion, a first separator middle portion, and a first separator bottom portion. The second separator comprises a second separator top portion, a second separator middle portion, and a second separator residual portion. The inlet receives feedstock and is in fluid communication with the first chemical reformer. The first chemical reformer bottom portion is in fluid communication with the second chemical reformer bottom portion through the first chemical reformer-second chemical reformer connector. The first chemical reformer top portion is in fluid communication with the first cooler through the first chemical reformer-first cooler connector. The second chemical reformer bottom portion is in fluid communication with the third chemical reformer bottom portion through the second chemical reformer-third chemical reformer connector. The second chemical reformer top portion is in fluid communication with the first cooler through the second chemical reformer-first cooler connector. The third chemical reformer top portion is in fluid communication with the first cooler through the third chemical reformer-first cooler connector. The first cooler is in fluid communication with the first separator through the first cooler-first separator connector. The first separator top portion is in fluid communication with the first separator vapor outlet. The first separator middle portion is in fluid communication with the first separator nonpolar outlet. The first separator bottom portion is in fluid communication with the first separator polar outlet. The third chemical reformer is in fluid communication with the second cooler through the third chemical reformer-second cooler connector. The second cooler is in fluid communication with the second separator through the second cooler-second separator connector. The second separator top portion is in fluid communication with the second separator light nonpolar outlet. The second separator middle portion is in fluid communication with the second separator medium nonpolar outlet. The second separator residual portion is in fluid communication with the second separator heavy nonpolar outlet.

In another embodiment of the present invention, the chemical reformer system may further comprise a control system. The control system is configured to control a first chemical reformer pressure through the first chemical reformer pressure regulator. The control system is configured to control a first chemical reformer temperature through the first chemical reformer temperature regulator. The control system is configured to control a second chemical reformer pressure through the second chemical reformer pressure regulator. The control system is configured to control a second chemical reformer temperature through the second chemical reformer temperature regulator. The control system is configured to control a third chemical reformer pressure through the third chemical reformer pressure regulator. The control system is configured to control a third chemical reformer temperature through the third chemical reformer temperature regulator.

In yet another embodiment of the present invention, the first chemical reformer pressure is greater than the second chemical reformer pressure. The second chemical reformer pressure is greater than the third chemical reformer pressure. The first chemical reformer chemical reformer temperature is less than the second chemical reformer temperature. The second chemical reformer temperature is less than the third chemical reformer temperature.

In an embodiment of the present invention, a chemical reformer system comprises an inlet, a plurality of chemical reformers connected in a series, a first cooler, a first separator, a first cooler-first separator connector, a first separator vapor outlet, a first separator nonpolar outlet, a first separator polar outlet, a second cooler, a last chemical reformer-second cooler connector, a second separator, a second cooler-second separator connector, a second separator light nonpolar outlet, a second separator medium nonpolar outlet, a second separator heavy nonpolar outlet, and a first separator-second separator connector. Each of the plurality of chemical reformers comprise a top portion, a bottom portion, a pressure regulator, and a temperature regulator. The first separator comprises a first separator top portion, a first separator middle portion, and a first separator bottom portion. The second separator comprises a second separator top portion, a second separator middle portion, and a second separator residual portion. The inlet receives feedstock and is in fluid communication with a first chemical reformer of the series. The plurality of chemical reformers are in fluid communication in the series through the bottom portions through chemical reformer connectors. The top portions of each of the plurality of chemical reformers are in fluid communication with the first cooler through chemical reformer-first cooler connectors. The first cooler is in fluid communication with the first separator through the first cooler-first separator connector. The first separator top portion is in fluid communication with the first separator vapor outlet. The first separator middle portion is in fluid communication with the first separator nonpolar outlet. The first separator bottom portion is in fluid communication with the first separator polar outlet. A last chemical reformer in the series is in fluid communication with the second cooler through the last reformer-second cooler connector. The second cooler is in fluid communication with the second separator through the second cooler-second separator connector. The second separator top portion is in fluid communication with the second separator light nonpolar outlet. The second separator middle portion is in fluid communication with the second separator medium nonpolar outlet. The second separator residual portion is in fluid communication with the second separator heavy nonpolar outlet.

In another embodiment of the present invention, the chemical reformer system may further comprise a control system. The control system is configured to control each pressure of the plurality of chemical reformers through its respective pressure regulator. The control system is configured to control each temperature of the plurality of chemical reformers through its respective temperature regulator.

In yet another embodiment of the present invention, the pressure decreases in the series of chemical reformers from the first chemical reformer to the last chemical reformer. The temperature increases in the series of chemical reformers from the first chemical reformer to the last chemical reformer.

BRIEF DESCRIPTION OF THE SEVERAL VIEWS OF THE DRAWING

The advantages and features of the present invention will be better understood as the following description is read in conjunction with the accompanying drawings, wherein.

Figure 1:
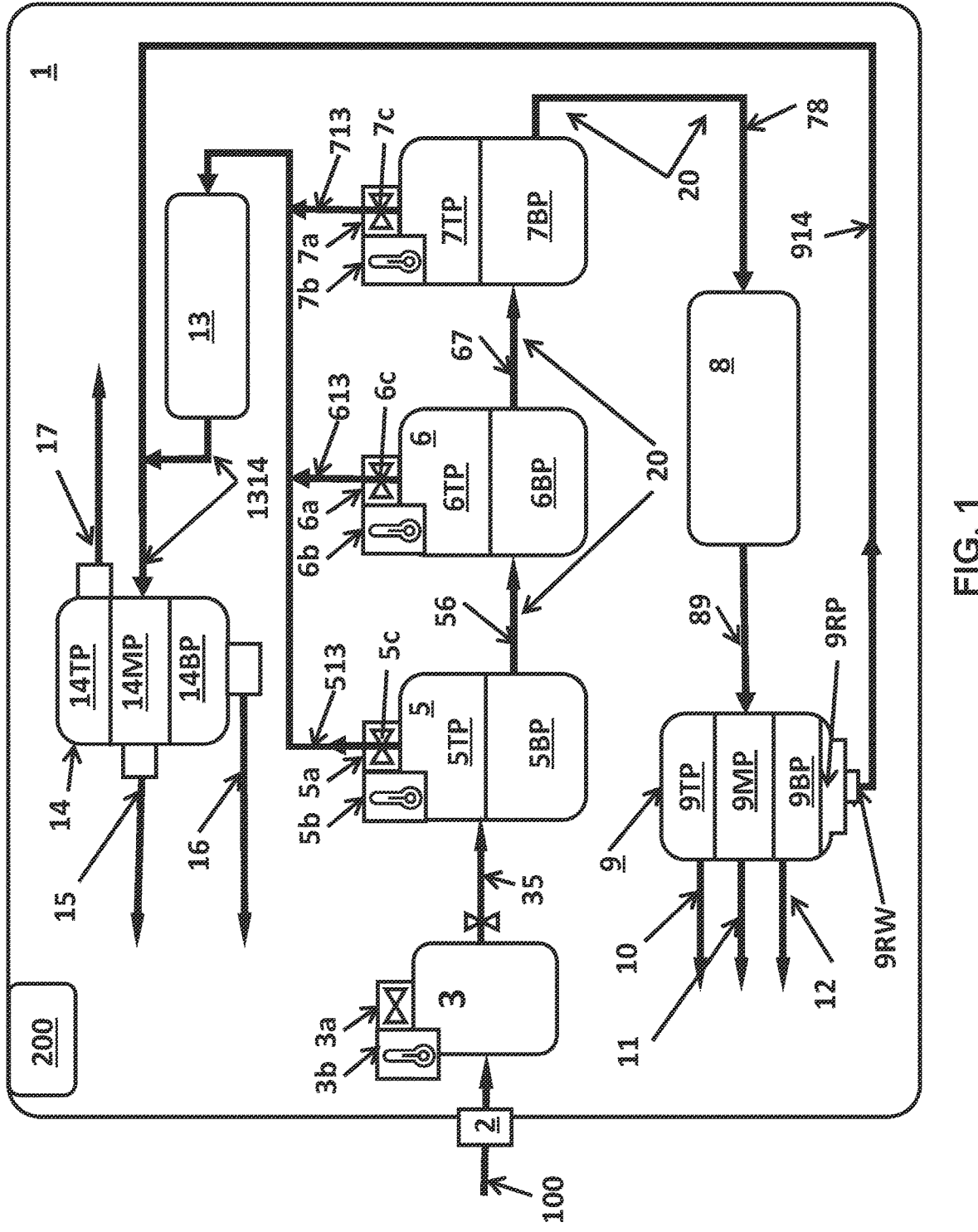
FIG. 1 is a diagram of an embodiment of the present invention.

For clarity purposes, all reference numerals may not be included in every figure.

DETAILED DESCRIPTION OF THE INVENTION

Temperature and rate of heating (or temperature increase) influence the operation of the chemical reformer and its conversion of feedstock biomass to output compounds, such as bio-oils. The temperatures of the various reactions determine the depolymerization of the biomass into bio-oils, as well as the repolymerization into char. The reaction temperatures are dependent on the feedstock. The rate of heating also can play an important role and influences the production of the different phase streams. Generally high heating rates can increase the production of liquid bio-oil, and heating rates above certain thresholds may inhibit production of certain liquids and production of certain gas phase streams. Pressure combined with temperature can be used to yield the desirable output compounds, such as oils, gases, chemicals, char, and others.

Feedstock can be any biomass, including biomasses from forestry and agriculture residues, sewage sludges, food process wastes, algae, industrial waste, rubbers, plastics, coal. The composition of the feedstock, including content of cellulose, hemicellulose, protein, lignin, minerals, fillers, and other compounds, can influence the yield and quality of resulting products, such as oils, fatty acids, and others.

Figure 2:
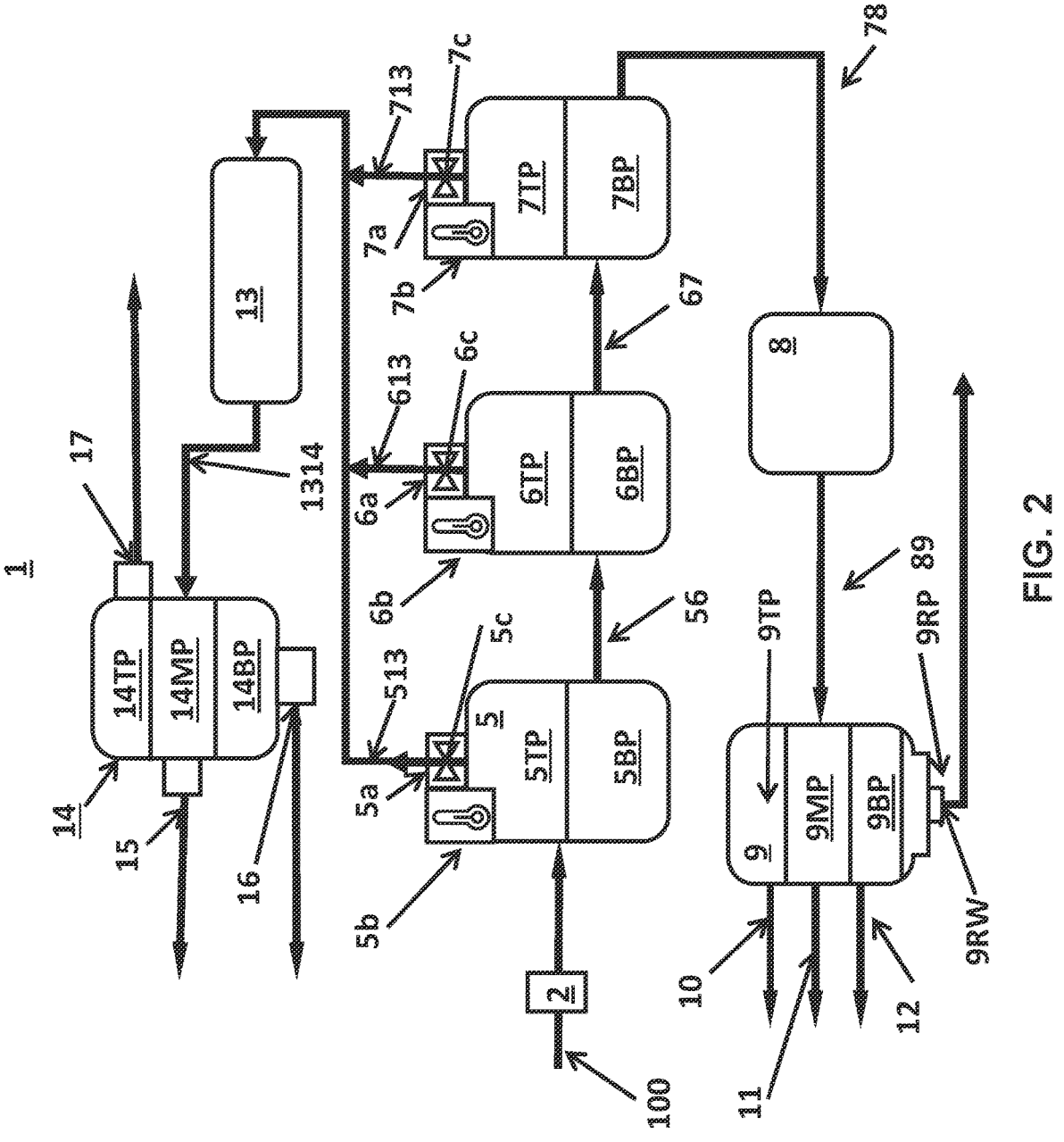
FIG. 2 is a diagram of an embodiment of the present invention.

As illustrated by the embodiments in FIGS. 1 and 2, the present invention is directed to a configurable chemical reformer system that can process a wide range of feedstocks and produce a wide variety of output products, depending on configuration of the system parameters, arrangement of the components, and the steps through which the feedstock is processed. The present invention can process feedstocks that are light and rich in lignocellulose, and can also be configured to process heavy petroleum, asphaltene residuals and coals of any type, polymerized feedstock (e.g., plastics), tires, and various others. Embodiments of the present invention enable feedstock from a relatively lower pressure Hydrothermal liquefaction to be processed through various digestion, reforming, and other vessels to produce an environment that is more conducive to the steam water shift reactions that produce hydrocarbons.

For example, embodiments may enable shifting the lignins from plant waste into liquid fuels by first converting them to fatty acids. Adjustment of the operating parameters, preferably temperature and pressure with a control system, can influence the reactions and change the resulting products. Adjusting the availability of free water in the process environment can also influence the reaction and the resulting products. Choice of feedstock will also result in different output products. For example, feedstock from animal processing facilities waste streams will allow the production of proteins, amino acids, nucleic acids and free fatty acids. Various resulting products can be purified by use of extraction with a non-polar solvent followed by molecular distillation.

Output products can be a wide range of free fatty acids, simple sugars, proteins, amino acids and nucleic acids to name a few, fuels and bio-oils of various weight and density. As an example, changing the parameters in any of the chemical reformers the system can be configured to shift the output product from one type to another, for example, fatty acids can be shifted to aldehydes, and even to hydrocarbons.

Figure 3:
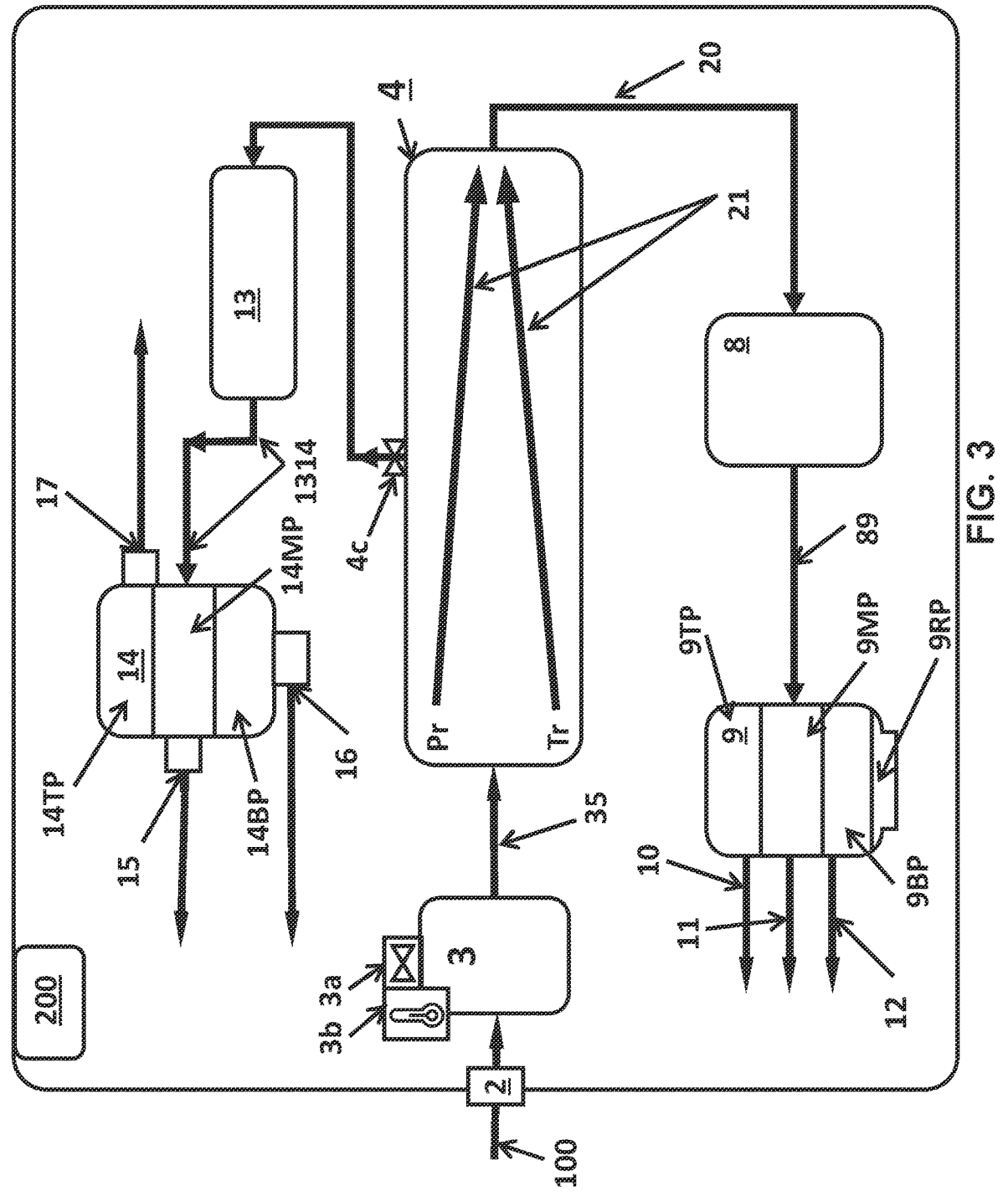
FIG. 3 is a diagram of an embodiment of the present invention.

As illustrated by the embodiment in FIG. 3, a system 1 according to the present invention receives feedstock 100, and processes it through various vessels, tanks, devices, or sections with configurable parameters. For example, in the embodiment shown in FIG. 3, feedstock 100 may be received at inlet 2 and transferred to a digester 3, from where the feedstock advances to a chemical reformer sequence 4. In another embodiment, the feedstock 100 is received into the sequence of chemical reformers 4, without passing through a digester 3. The chemical reformer sequence 4 may comprise a plurality of chemical reforming steps whose number may be limited only by practical considerations and cost. In the chemical reforming sequence 4, generally the reforming temperature Tr during each chemical reforming step increases with each step, while the reforming pressure Pr decreases with each step, as illustrated by arrow lines 21 (i.e., the chemical reformers are connected in a series from the first chemical reformer in the series to the last chemical reformer in the series). The chemical reforming sequence may comprise a vapor valve 4c configured to release any vapors from the chemical reformers if the vapor pressure exceeds a pressure setpoint.

The physical environment of increasing temperature Tr and decreasing pressure Pr influences the water shift reactions causing the polymerization bonds in biomass to break, reforming the feedstock 100 into hydrocarbon molecules with varying length and complexity, all of which are lighter than water. While the water shift reactions are responsible for the hydrocarbon formation, the temperature Tr, and inverse pressure gradient Pr determine the variety and density of the final products. The physical environment may be varied by increasing the number of chemical reforming steps (or chemical reformers) 4, so that the increase in Tr and decrease in Pr will be small from one reformer step to the next. Or the number of chemical reformer steps can be reduced, increasing the step change in Tr and Pr between chemical reforming steps.

In addition, the start Temperature Tr and Pressure Pr in the first chemical reformer (or chemical reforming step) and the end Temperature Tr and Pressure Pr in the last chemical reformer (or chemical reforming step) may be selected depending on the type of feedstock 100, and to influence the type of hydrocarbon resulting product from the system.

Upon completion of the chemical reforming sequence 4, the reformed process material can be transferred to one or more cooling steps 8, 13, and then to one or more separation steps 9, 14, to extract desired output hydrocarbon products.

As shown in FIGS. 1, 2, 3, embodiments of the present invention can be chemical reformer systems 1 comprising an inlet 2, a first chemical reformer 5, a first chemical reformer-second chemical reformer connector 56, a second chemical reformer 6, a second chemical reformer-third chemical reformer connector 67, a third chemical reformer 7, a first cooler 13, a first chemical reformer-first cooler connector 513, a second chemical reformer-first cooler connector 613, a third chemical reformer-first cooler connector 713, a first separator 14, a first cooler-first separator connector 1314, a first separator vapor outlet 17, a first separator nonpolar outlet 15, a first separator polar outlet 16, a second cooler 8, a third chemical reformer-second cooler connector 78, a second separator 9, a second cooler-second separator connector 89, a second separator light nonpolar outlet 10, a second separator medium nonpolar outlet 11, a second separator heavy nonpolar outlet 12, a second separator polar outlet 9RW, and a first separator-second separator connector 914.

System 1 may also comprise a digester 3, a digester pressure regulator 3a, a digester temperature regulator 3b, and a digester-first chemical reformer connector 35.

The first chemical reformer 5 comprises a first chemical reformer top portion 5TP a first chemical reformer bottom portion 5BP, a first chemical reformer pressure regulator 5a, a first chemical reformer vapor valve 5c, and a first chemical reformer temperature regulator 5b. The second chemical reformer 6 comprises a second chemical reformer top portion 6TP, a second chemical reformer bottom portion 6BP, a second chemical reformer pressure regulator 6a, a second chemical reformer vapor valve 6c, and a second chemical reformer temperature regulator 6b. The third chemical reformer 7 comprises a third chemical reformer top portion 7TP, a third chemical reformer bottom portion 7BP, a third chemical reformer pressure regulator 7a, a third chemical reformer vapor valve 7c, and a third chemical reformer temperature regulator 6b.

The first separator 14 comprises a first separator top portion 14TP a first separator middle portion 14MP and a first separator bottom portion 14BP. The second separator 9 comprises a second separator top portion 9TP, a second separator middle portion 9MP, a second separator bottom portion 9BP, and a second separator residual portion 9RP.

The inlet 2 receives feedstock 100. In the embodiment illustrated in FIG. 1, the inlet 2 is in fluid communication with the digester 3. The digester 3 is in fluid communication with the first chemical reformer 5 through the digester-first chemical reformer connector 35. In the embodiment illustrated in FIG. 2, the Inlet 2 is in fluid communication with the first chemical reformer 5.

The first chemical reformer bottom portion 5BP is in fluid communication with the second chemical reformer bottom portion 6BP through the first chemical reformer-second chemical reformer connector 56. The first chemical reformer top portion 5TP is in fluid communication with the first cooler 13 through the first chemical reformer-first cooler connector 513. The second chemical reformer bottom portion 6BP is in fluid communication with the third chemical reformer bottom portion 7BP through the second chemical reformer-third chemical reformer connector 67. The second chemical reformer top portion 6TP is in fluid communication with the first cooler 13 through the second chemical reformer-first cooler connector 613. The third chemical reformer top portion 7TP is in fluid communication with the first cooler 13 through the third chemical reformer-first cooler connector 713. The first cooler 13 is in fluid communication with the first separator 14 through the first cooler-first separator connector 1314. The first separator top portion 14TP is in fluid communication with the first separator vapor outlet 17. The first separator middle portion 14MP is in fluid communication with the first separator nonpolar outlet 15. The first separator bottom portion 14BP is in fluid communication with the first separator polar outlet 16.

The third chemical reformer 7 is in fluid communication with the second cooler 8 through the third chemical reformer-second cooler connector 78. The second cooler 8 is in fluid communication with the second separator 9 through the second cooler-second separator connector 89. The second separator top portion 9TP is in fluid communication with the second separator light nonpolar outlet 10. The second separator top-middle portion 9MP is in fluid communication with the second separator medium nonpolar outlet 11. The second separator middle-bottom portion 9BP is in fluid communication with the second separator heavy nonpolar outlet 12. The second separator residual portion 9RP is in fluid communication with the second separator polar outlet 9RW.

The first and second coolers 13, 8, may each comprise temperature regulators 13b, 8b, to control the temperature to which the materials in each cooler 13, 8, and at which the materials will be transferred to the first and second separators 14, 9.

The chemical reformer system may further comprise a control system 200 which may be configured to control the digester pressure through the digester pressure regulator 3a, to control the digester temperature through the digester temperature regulator 3b, to control the first chemical reformer pressure through the first chemical reformer pressure regulator 5a, to control the first chemical reformer temperature through the first chemical reformer temperature regulator 5b, to control the second chemical reformer pressure through the second chemical reformer pressure regulator 6a. to control the second chemical reformer temperature through the second chemical reformer temperature regulator 6b, to control the third chemical reformer pressure through the third chemical reformer pressure regulator 7a, and to control the third chemical reformer temperature through the third chemical reformer temperature regulator 7b. Control system 200 may be configured to control the cooling temperature in the first and second coolers 13, 8, through the first and second cooler temperature regulators 13b, 8b.

Control system 200 may be configured to enable an operator to configure temperature and pressure setpoints for each of the digester 3, chemical reformers 5, 6, 7, coolers 8, 13, and separators 9, 14.

Digester pressure regulator 3a may comprise one or more valves (not shown), pressure gauges or sensors (not shown), and/or pumps (not shown) that control the pressure of the feedstock 100 in digester 3. The valves, gauges, and/or pumps may be mounted on one or more of the digester 3, the inlet 2, and connector 35. Chemical reformer pressure regulators 5a, 6a, 7b may comprise vapor valves 5c, 6c, 7c, one or more other valves (not shown), pressure sensors (not shown), and/or pumps (not shown) that control the reforming pressure Pr in each of the chemical reformers 5, 6, 7. The one or more other valves, the pressure gauges, and/or the pumps may be located on one or more of the chemical reformers 5, 6, 7, and the connectors 35, 56, 67, 78, 513, 613, 713.

Digester temperature regulator 3b may comprise temperature sensors and heating elements mounted on one or more of the digester 3, the inlet 2, and the connector 35. Chemical reformer temperature regulators 5b, 6b, 7b, may comprise temperature sensors and heating elements mounted on one or more of chemical reformers 5, 6, 7, inlet 2, and connectors 35, 56, 67. Cooler temperature regulators 8b, 13b, may comprise temperature sensors and/or actuating devices (influencing, e.g., cooling medium flow, heat exchanger flow), connector controls (e.g., causing the transfer through a connector of fluid upon reaching the desired temperature). Given the strong interaction between temperature and pressure in fluids, temperature regulators and pressure regulators may interact through control system 200 to maintain desired temperature and pressures.

In the above descriptions the term cooler generally indicates a cooling section or portion of system 1 configured to cool a fluid, and may be a separate cooling vessel, or a portion of another vessel, tank, or device. The terms cooler, cooler, and cooling vessel are used interchangeably within this description. Similarly, the terms separator, separation section, separation vessel, and similar terms are used interchangeably to identify a tank, device, portion, or section within system 1 configured to enable separation of the processed material based on various factors, such as weight, specific gravity, solubility, phase, and others.

The terms reformer, chemical reformer, reformer section, reformer vessel, are similar used interchangeably, to designate a device, section, or a portion of system 1 configured to reform the hydrocarbons in the feedstock by altering, modifying, or rearranging their molecular structure and/or altering their properties.

Below, embodiments of the present invention are described with additional details, and with reference to specific temperature and pressure setpoints as examples, to illustrate the operation of the present invention. The specific examples are provided solely as examples and should not be construed as limiting. The specific parameters can be selected by an operator to configure the system to produce the desired types of product streams based on the feedstock.

An embodiment of the present invention, for example illustrated in FIG. 1, can be well suited for processing feedstock that is high in lignocellulose, comprising, for example, cellulose, hemicellulose, and lignins. The feedstock may be coming from an aerobic digester, an anaerobic digester, or previous thermal treatment. Feedstock, or process material, 100 is fed through an inlet 2 into a digestion vessel ("digester") 3 where the feedstock may be subjected to a mild digestion reaction with an alkaline compound, for example, sodium hydroxide (NaOH) while being subjected to thermal treatment under a controlled temperature. Digester temperature regulator 3b may be configured to maintain the temperature in digester 3, preferably at about 150 C, which can result in the production of fatty acids from the lignin in the feedstock. Other digestion temperatures (e.g., 170 C, 200 C, etc.), or bases other than NaOH may be used in digester 3, to alter the rates of production of fatty acids, to influence the production of different types of fatty acids, or may result in the production of different compounds. Pressure in Digester 3 may also be regulated by digester-pressure regulator 3a to influence the digestion of lignocellulose in the feedstock. Also, digester-pressure regulator 3a and digester-temperature regulator 3b may be configured to work together to maintain a desired digestion temperature and pressure.

The material treated in digester 3 may be reformed (e.g., altering properties, rearranging molecular structure) through multiple reformers subjecting the organic process material to various water-shift reactions. In a preferred embodiment, the reforming temperature increases with each subsequent reformer, while the reforming pressure decreases. The increasing temperature and decreasing pressure reforms the hydrocarbon to shift toward lighter API gravity (American Petroleum Institute Gravity) ("API"), or lower density hydrocarbons. Preferred embodiments illustrating specific temperature and pressure setpoints are described below. The examples here should not be construed as limiting, as it will be well understood that the present invention can be utilized to produce different materials, and materials with varying APIs, by varying the temperature and pressure setpoints in each reforming step, varying the rates of temperature and/or pressure changes, and incorporating more or less reforming steps than in the examples herein.

The process material 100 is transferred from digester 3 to a first reformer 5 through a digester-first reformer pipe connector 35. A first reformer temperature regulator 5b and a first reformer pressure regulator 5a may be configured to maintain the temperature and pressure setpoints in reformer 5 to facilitate reforming of the hydrocarbons present in reformer 5. In a preferred embodiment, reformer 5 is maintained at a temperature of about 180 C at a pressure of around 250 psi.

The organic process material is transported from first reformer 5 to second reformer 6 through a first reformer-second reformer pipe connection 56. A second reformer temperature regulator 6b and a second reformer pressure regulator 6a may be configured to maintain the temperature and pressure setpoints in reformer 6 to facilitate reforming of the hydrocarbons in the material. In a preferred embodiment, reformer 6 is maintained at a temperature of about 200 C at a pressure of around 150 psi.

From second reformer 6, the organic process material is transferred to the third reformer 7, through the second reformer-third reformer pipe connector 67. A second reformer temperature regulator 7b and a second reformer pressure regulator 7a may be configured to maintain the temperature and pressure setpoints in reformer 6 preferably at a temperature of about 400 C at a pressure of around 50 psi.

Reforming the organic process material in the reformers 5, 6, 7 may produce vapor thereby increasing the vapor pressure in the reformers 5, 6, 7. To maintain the desired reforming pressure and/or temperature, reformers 5, 6, 7, may be equipped with vapor valves 5c, 6c, 7c, configured to release vapor into pipe connectors 513, 613, 713, if the vapor pressure exceeds a desired pressure setpoint. Valves 5, 6c, 5c, may be part of, or work coordinately with, reformer pressure regulators 5a, 6a, 7b. Vapor released from vapor valves 5c, 6c, 7c is transported through pipe connectors 513, 613, 713 to a first cooler 13. Upon reducing the temperature of the vapor in cooler 13 using well known cooling methods (e.g., direct or indirect heat exchange; cooling media such as air, water, other fluids; others) the resulting cooled fluid is transferred through pipe connector 1314 to first separator 14.

After the reforming steps the reformed liquid 20 remaining in reformers 5, 6, 7, may comprise reformed hydrocarbon compounds that may be highly desirable as fuels (e.g., around 40 API), as well as other compounds. In general, the reformed liquid 20 may be a liquid mechanical mixture comprising heavy, medium, and light oils.

Through a third reformer-second cooler pipe connector 78 the reformed liquid 20 is transferred to a second cooler, cooler, or a cooling vessel, 8, where the re-formed liquid 20 is cooled using well known methods, including direct or indirect heat exchange, using various cooling media (e.g., air, water, other fluids), cooling towers, and others.

From the second cooler 8, the reformed liquid 20 is transferred to a second separator vessel, a separating station, or for simplicity a "separator" 9, where the reformed liquid is separated into multiple compounds based on their weight, which my correspond to the compounds' molecular weight, specific gravity, or density. In one example, the bio-oil compounds may be separated according to their specific gravity into "light" bio-oils, "medium" weight bio-oils, and "heavy" bio-oils. The second separator 9 may be configured to accumulate the light bio-oils in the second separator top portion 9TP, the medium oils in the second separator middle portion 9MP, and the heavy oils in the second separator bottom portion 9BP. Because all the bio-oils in second separator 9 are lighter than water, any residual liquid water that may accumulate beneath the heavy oils in a second separator residual portion 9RP.

Second separator 9 may then be configured to expel the "light" compounds in the top portion 9TP through a second separator light nonpolar outlet 10, the "medium" compounds in the second separator middle portion 9MP through a second separator medium nonpolar outlet 11, and the "heavy" compounds in the second separator bottom portion 9BP through a second separator heavy nonpolar outlet 12. Residual water that may be collected in the second separator residual portion 9RP may be expelled through the second separator polar outlet 9RW.

The cooled fluid in first separator 14 may contain hydrocarbons that escaped with the vapor from reformers 5, 6, 7. Those hydrocarbons, with vapor points coinciding with the temperature and pressure setpoints in each of the first reformer 5, second reformer 6, and third reformer 7. Upon cooling the vapor in cooler 13 some of escaped hydrocarbons may become liquids and some may remain gaseous, resulting in a cooled fluid in separator 14 comprising gaseous hydrocarbons, liquid hydrocarbons, and water. The liquid hydrocarbons in separator 14 generally will fall in the "light" oils category, and the gaseous hydrocarbons, generally will be gas fuels, such as biogas or other gas fuels. First separator 14 is configured to separate the water from the cooled fluid into a separator bottom portion 14BP, the light oils into a separator middle portion 14MP, and the gas phase, or gas fuels, into a separator top portion 14TP. Light oils collected in the first separator middle portion 14MP can be expelled through the first separator polar outlet 15, and if desired, may be combined with the light oils expelled from second separator light poler outlet 10. Gas fuels collected in the first separator top portion 14TP may be expelled through the first separator gas outlet 17 and used for power generation, heat production, or other needs. Water collected in the first separator bottom portion 14BP may be expelled through the first separator nonpolar outlet 15, and reused for further processing, or directed to wastewater treatment system.

An embodiment illustrated in FIG. 2, may be better suited to process feedstock that has been polymerized into (e.g., plastic), as well as heavy petroleum, tires, asphaltene residuals and coals of any type, including feedstock from a high moisture thermal treatment. This embodiment may be combined with hydrocracking and hydrogenation to make even lighter products.

In one example, feedstock, or process material, 100 may be at a temperature of around 500 F and at a pressure of 600-700 psi as it enters inlet 2, and proceeds into the sequence of chemical reforming steps in reformers 5, 6, 7 where conditions may be configured for water shift reactions to break the polymerization bonds and reform the process material 100 into less complex molecules and/or shorter molecular sequences. In the first reformer 5, the process material is at approximately 600 F and 500 psi. Process materials are transferred through connector 56 to the second reformer 6, which may be maintained at a temperature of approximately 700 F and pressure of approximately 350 psi. In second reformer 6, the process material is reformed to form smaller molecules and shorter molecular sequences. From second reformer 6 the process material 100 is transferred into the third reforming step, reformer 7, where the process materials may be maintained at a temperature of approximately 800 F and pressure of approximately 100 psi, forming the shortest molecular sequences and the smallest molecules.

The environment in reformers 5, 6, 7, may be maintained in such a way, so that the moisture level, which is directly related to the pressure in the sequenced reformers 5, 6, 7, is continually being lowered, the moisture that is providing the pressure is relieved as the process material passes from reformer 5 to reformer 6, and from reformer 6, to reformer 7. Vapor, combing moisture and hydrocarbons with vapor stages at the temperatures and pressures of the reformers 5, 6, 7, is removed through the vapor valves 5c, 6c, and 7c, and transported through connectors 513, 613, and 713 to first cooler 13. In the first cooler 13, the vapor is cooled to condense into a cooled fluid comprising water and hydrocarbons. The cooled fluid is transferred through connector 1314 into the first separator 14 where the fluid may be separated into liquid and gas phases based on a desired vapor stage of any present hydrocarbons. An operator may control the vapor stage separation threshold by altering the temperature and pressure settings for first separator 14. The vapor phase may be expelled through the first separator vapor outlet 17. The liquid hydrocarbon phase can be transferred through the first separator polar outlet 15. The water in the first separator bottom portion 14BP transfers out through the first separator nonpolar outlet 16 and may be reused for hydrothermal liquefaction processes or treated for discharge.

The reformed liquid 20 exits the third reformer 7 and is transferred through connector 78 into the second cooler 8, where it is cooled before being transferred into the second separator 9. In the second cooler the reformed liquid may be cooled to anywhere between 70 F to 370 F depending on the type of separation (e.g., distillation, stratification, etc.) to be used in the second separator 9. In separator 9, the reformed hydrocarbons from reformed liquid 20 may be separated according to weight or vapor stage (if distillation). In one embodiment, the second separator light nonpolar outlet 10 may expel light oils similar to kerosene, the second separator medium nonpolar outlet 11 may expel medium oils similar to diesel, and the second separator heavy nonpolar outlet 12 may expel heavy oil that can be used as a burner fuel. In this embodiment, due to the high temperatures and pressures in reformers 5, 6, 7, reformed liquid 20 should not contain water (in any phase) and accordingly there should be no residual water to dispose of from the second separator 9. Reformed liquid 20 may contain some minerals and/or fillers which may settle and separate from hydrocarbons in the second separator residual portion 9RP and then can be expelled through the second separator polar outlet 9RW.

While the invention has been described with reference to exemplary embodiments it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiments disclosed as the best mode contemplated for carrying out this invention, but that the invention will include all embodiments falling within the scope of the appended claims. Moreover, unless specifically stated, any use of the terms first, second, etc., do not denote any order or importance but rather the terms first, second, etc., are used to distinguish one element from another.

I claim:

1. A chemical reformer system comprising:

an inlet;

a digester;

a digester pressure regulator;

a digester temperature regulator;

a digester-first chemical reformer connector;

a first chemical reformer;

wherein the first chemical reformer comprises:

a first chemical reformer top portion;

a first chemical reformer bottom portion;

a first chemical reformer pressure regulator; and, a first chemical reformer temperature regulator;

a first chemical reformer-second chemical reformer connector;

a second chemical reformer;

wherein the second chemical reformer comprises:

a second chemical reformer top portion;

a second chemical reformer bottom portion;

a second chemical reformer pressure regulator; and, a second chemical reformer temperature regulator;

a second chemical reformer-third chemical reformer connector;

a third chemical reformer;

wherein the third chemical reformer comprises:

a third chemical reformer top portion;

a third chemical reformer bottom portion;

a third chemical reformer pressure regulator; and, a third chemical reformer temperature regulator;

a first cooler;

a first chemical reformer-first cooler connector;

a second chemical reformer-first cooler connector;

a third chemical reformer-first cooler connector;

a first separator;

wherein the first separator comprises:

a first separator top portion;

a first separator middle portion; and, a first separator bottom portion;

a first cooler-first separator connector;

a first separator vapor outlet;

a first separator nonpolar outlet;

a first separator polar outlet;

a second cooler;

a third chemical reformer-second cooler connector;

a second separator;

wherein the second separator comprises:

a second separator top portion;

a second separator middle portion;

a second separator bottom portion; and, a second separator residual portion;

a second cooler-second separator connector;

a second separator light nonpolar outlet;

a second separator medium nonpolar outlet;

a second separator heavy nonpolar outlet;

a second separator polar outlet; and, a first separator-second separator connector;

wherein the inlet receives feedstock;

wherein the inlet is in fluid communication with the digester;

wherein the digester is in fluid communication with the first chemical reformer through the digester-first chemical reformer connector;

wherein the first chemical reformer bottom portion is in fluid communication with the second chemical reformer bottom portion through the first chemical reformer-second chemical reformer connector;

wherein the first chemical reformer top portion is in fluid communication with the first cooler through the first chemical reformer-first cooler connector;

wherein the second chemical reformer bottom portion is in fluid communication with the third chemical reformer bottom portion through the second chemical reformer-third chemical reformer connector;

wherein the second chemical reformer top portion is in fluid communication with the first cooler through the second chemical reformer-first cooler connector;

wherein the third chemical reformer top portion is in fluid communication with the first cooler through the third chemical reformer-first cooler connector;

wherein the first cooler is in fluid communication with the first separator through the first cooler-first separator connector;

wherein the first separator top portion is in fluid communication with the first separator vapor outlet;

wherein the first separator middle portion is in fluid communication with the first separator nonpolar outlet;

wherein the first separator bottom portion is in fluid communication with the first separator polar outlet;

wherein the third chemical reformer is in fluid communication with the second cooler through the third chemical reformer-second cooler connector;

wherein the second cooler is in fluid communication with the second separator through the second cooler-second separator connector;

wherein the second separator top portion is in fluid communication with the second separator light nonpolar outlet;

wherein the second separator middle portion is in fluid communication with the second separator medium nonpolar outlet;

wherein the second separator bottom portion is in fluid communication with the second separator heavy nonpolar outlet; and, wherein the second separator residual portion is in fluid communication with the second separator polar outlet.

2. The chemical reformer system of claim 1 further comprising:

a control system;

wherein the control system is configured to control a digester pressure through the digester pressure regulator;

wherein the control system is configured to control a digester temperature through the digester temperature regulator;

wherein the control system is configured to control a first chemical reformer pressure through the first chemical reformer pressure regulator;

wherein the control system is configured to control a first chemical reformer temperature through the first chemical reformer temperature regulator;

wherein the control system is configured to control a second chemical reformer pressure through the second chemical reformer pressure regulator;

wherein the control system is configured to control a second chemical reformer temperature through the second chemical reformer temperature regulator;

wherein the control system is configured to control a third chemical reformer pressure through the third chemical reformer pressure regulator; and, wherein the control system is configured to control a third chemical reformer temperature through the third chemical reformer temperature regulator.

3. The chemical reformer of claim 2, wherein the first chemical reformer pressure is greater than the second chemical reformer pressure;

wherein the second chemical reformer pressure is greater than the third chemical reformer pressure;

wherein the first chemical reformer chemical reformer temperature is less than the second chemical reformer temperature; and, wherein the second chemical reformer temperature is less than the third chemical reformer temperature.

4. A chemical reformer system comprising:

an inlet;

a first chemical reformer;

wherein the first chemical reformer comprises:

a first chemical reformer top portion;

a first chemical reformer bottom portion;

a first chemical reformer pressure regulator; and, a first chemical reformer temperature regulator;

a first chemical reformer-second chemical reformer connector;

a second chemical reformer;

wherein the second chemical reformer comprises:

a second chemical reformer top portion;

a second chemical reformer bottom portion;

a second chemical reformer pressure regulator; and, a second chemical reformer temperature regulator;

a second chemical reformer-third chemical reformer connector;

a third chemical reformer;

wherein the third chemical reformer comprises:

a third chemical reformer top portion;

a third chemical reformer bottom portion;

a third chemical reformer pressure regulator; and, a third chemical reformer temperature regulator;

a first cooler;

a first chemical reformer-first cooler connector;

a second chemical reformer-first cooler connector;

a third chemical reformer-first cooler connector;

a first separator;

wherein the first separator comprises:

a first separator top portion;

a first separator middle portion; and, a first separator bottom portion;

a first cooler-first separator connector;

a first separator vapor outlet;

a first separator nonpolar outlet;

a first separator polar outlet;

a second cooler;

a third chemical reformer-second cooler connector;

a second separator;

wherein the second separator comprises:

a second separator top portion;

a second separator middle portion; and, a second separator residual portion;

a second cooler-second separator connector;

a second separator light nonpolar outlet;

a second separator medium nonpolar outlet;

a second separator heavy nonpolar outlet; and,

16 a first separator-second separator connector;

wherein the inlet receives feedstock;

wherein the inlet is in fluid communication with the first chemical reformer;

wherein the first chemical reformer bottom portion is in fluid communication with the second chemical reformer bottom portion through the first chemical reformer-second chemical reformer connector;

wherein the first chemical reformer top portion is in fluid communication with the first cooler through the first chemical reformer-first cooler connector;

wherein the second chemical reformer bottom portion is in fluid communication with the third chemical reformer bottom portion through the second chemical reformer-third chemical reformer connector;

wherein the second chemical reformer top portion is in fluid communication with the first cooler through the second chemical reformer-first cooler connector;

wherein the third chemical reformer top portion is in fluid communication with the first cooler through the third chemical reformer-first cooler connector;

wherein the first cooler is in fluid communication with the first separator through the first cooler-first separator connector;

wherein the first separator top portion is in fluid communication with the first separator vapor outlet;

wherein the first separator middle portion is in fluid communication with the first separator nonpolar outlet;

wherein the first separator bottom portion is in fluid communication with the first separator polar outlet;

wherein the third chemical reformer is in fluid communication with the second cooler through the third chemical reformer-second cooler connector;

wherein the second cooler is in fluid communication with the second separator through the second cooler-second separator connector;

wherein the second separator top portion is in fluid communication with the second separator light nonpolar outlet;

wherein the second separator middle portion is in fluid communication with the second separator medium nonpolar outlet; and, wherein the second separator residual portion is in fluid communication with the second separator heavy nonpolar outlet.

5. The chemical reformer system of claim 4 further comprising:

a control system;

wherein the control system is configured to control a first chemical reformer pressure through the first chemical reformer pressure regulator;

wherein the control system is configured to control a first chemical reformer temperature through the first chemical reformer temperature regulator;

wherein the control system is configured to control a second chemical reformer pressure through the second chemical reformer pressure regulator;

wherein the control system is configured to control a second chemical reformer temperature through the second chemical reformer temperature regulator;

wherein the control system is configured to control a third chemical reformer pressure through the third chemical reformer pressure regulator; and, wherein the control system is configured to control a third chemical reformer temperature through the third chemical reformer temperature regulator.

6. The chemical reformer of claim 5, wherein the first chemical reformer pressure is greater than the second chemical reformer pressure;

wherein the second chemical reformer pressure is greater than the third chemical reformer pressure;

wherein the first chemical reformer chemical reformer temperature is less than the second chemical reformer temperature; and, wherein the second chemical reformer temperature is less than the third chemical reformer temperature.

7. A chemical reformer system comprising:

an inlet;

a plurality of chemical reformers connected in a series;

wherein each of the plurality of chemical reformers comprise:

a top portion;

a bottom portion;

a pressure regulator; and, a temperature regulator;

a first cooler;

a first separator;

wherein the first separator comprises:

a first separator top portion;

a first separator middle portion; and, a first separator bottom portion;

a first cooler-first separator connector;

a first separator vapor outlet;

a first separator nonpolar outlet;

a first separator polar outlet;

a second cooler;

a last chemical reformer-second cooler connector;

a second separator;

wherein the second separator comprises:

a second separator top portion;

a second separator middle portion; and, a second separator residual portion;

a second cooler-second separator connector;

a second separator light nonpolar outlet;

a second separator medium nonpolar outlet;

a second separator heavy nonpolar outlet; and, a first separator-second separator connector;

wherein the inlet receives feedstock;

wherein the inlet is in fluid communication with a first chemical reformer of the series;

wherein the plurality of chemical reformers are in fluid communication in the series through the bottom portions through chemical reformer connectors;

wherein the top portions of each of the plurality of chemical reformers are in fluid communication with the first cooler through chemical reformer-first cooler connectors;

wherein the first cooler is in fluid communication with the first separator through the first cooler-first separator connector;

wherein the first separator top portion is in fluid communication with the first separator vapor outlet;

wherein the first separator middle portion is in fluid communication with the first separator nonpolar outlet;

wherein the first separator bottom portion is in fluid communication with the first separator polar outlet;

wherein a last chemical reformer in the series is in fluid communication with the second cooler through the last reformer-second cooler connector;

wherein the second cooler is in fluid communication with the second separator through the second cooler-second separator connector;

wherein the second separator top portion is in fluid communication with the second separator light nonpolar outlet;

wherein the second separator middle portion is in fluid communication with the second separator medium nonpolar outlet; and, wherein the second separator residual portion is in fluid communication with the second separator heavy nonpolar outlet.

8. The chemical reformer system of claim 7 further comprising:

a control system;

wherein the control system is configured to control each pressure of the plurality of chemical reformers through its respective pressure regulator; and, wherein the control system is configured to control each temperature of the plurality of chemical reformers through its respective temperature regulator.

9. The chemical reformer of claim 8, wherein the pressure decreases in the series of chemical reformers from the first chemical reformer to the last chemical reformer; and, wherein the temperature increases in the series of chemical reformers from the first chemical reformer to the last chemical reformer.

* * * * *